United States Patent
Burnside et al.

(10) Patent No.: US 6,811,794 B2
(45) Date of Patent: Nov. 2, 2004

(54) SUSTAINED RELEASE PHARMACEUTICAL DOSAGE FORMS WITH MINIMIZED PH DEPENDENT DISSOLUTION PROFILES

(75) Inventors: Beth A. Burnside, Bethesda, MD (US); Rong-Kun Chang, Rockville, MD (US); Xiaodi Guo, New City, NY (US)

(73) Assignee: Shire Laboratories, Inc., Rockville, MD (US)

( * ) Notice: Subject to any disclaimer, the term of this patent is extended or adjusted under 35 U.S.C. 154(b) by 196 days.

(21) Appl. No.: 10/027,349

(22) Filed: Dec. 20, 2001

(65) Prior Publication Data

US 2003/0158261 A1 Aug. 21, 2003

(51) Int. Cl.[7] ............................................... A61K 9/22
(52) U.S. Cl. ...................................................... 424/468
(58) Field of Search ......................................... 424/468

(56) References Cited

U.S. PATENT DOCUMENTS

| | | | |
|---|---|---|---|
| 4,968,508 A | 11/1990 | Oren et al. | 424/468 |
| 5,102,668 A | 4/1992 | Eichel et al. | 424/490 |
| 5,378,474 A | 1/1995 | Morella et al. | 424/469 |
| 6,287,599 B1 * | 9/2001 | Burnside et al. | 424/468 |
| 2004/0064800 A1 * | 4/2004 | Korobkov | 716/10 |

* cited by examiner

Primary Examiner—Alton Pryor
(74) Attorney, Agent, or Firm—M. Elisa Lane (57) ABSTRACT

A pharmaceutical composition comprising at least one pharmaceutically active agent that is pH dependent, at least one non-pH dependent sustained release agent, and at least one pH dependent agent that increases the dissolution rate of the at least one pharmaceutically active agent at a pH in excess of 5.5. Such compositions have minimized pH-dependent dissolution profiles or pH-independent dissolution profiles.

12 Claims, 2 Drawing Sheets

FIG. 1

Figure 2  Mean Anagrelide Plasma Concentrations (ng/mL) over Time following Oral Administration of 1 mg SPD 427 Formulations or Agrylin® Immediate-Release in Healthy, Fasted Adults (N=12)

SUSTAINED RELEASE PHARMACEUTICAL DOSAGE FORMS WITH MINIMIZED PH DEPENDENT DISSOLUTION PROFILES

This invention relates to pharmaceutical compositions. More particularly, this invention relates to pharmaceutical compositions having a pH-independent or a minimized pH-dependent dissolution profile. In particular, such composition includes at least one pharmaceutically active agent that has a pH dependent solubility profile, at least one non-pH-dependent sustained release agent, and at least one pH-dependent agent that increases the dissolution rate of the at least one pharmaceutically active agent at a pH in excess of 5.5. The active agent(s) has (have) a solubility profile wherein the active agent(s) is (are) more soluble in an acidic medium than in a basic medium.

The rate at which a drug goes into solution when it is dissolved in a medium is proportional to the solubility of the drug in the medium. Many drugs have different solubilities at different pHs. These pH-dependent solubility differences lead to pH-dependent dissolution profiles. In general, pH-dependent dissolution is an undesirable product characteristic.

Compressed matrix tablets containing a basic drug often give a faster dissolution profile in simulated gastric fluid, having a pH about 1.0, than in simulated intestinal fluid (pH 6.8 to 7.4).

It is an object of the present invention to provide a pharmaceutical composition with a minimized pH dependent or a pH-independent dissolution profile.

In accordance with an aspect of the present invention, there is provided a pharmaceutical composition. The composition comprises at least one pharmaceutically active agent that is pH dependent, at least one non-pH dependent sustained release agent, and at least one pH-dependent agent that increases the rate of release of the at least one pharmaceutically active agent from the tablet at a pH in excess of 5.5, such as at least one organic acid that maintains an acidic micro-environment in the tablet.

Pharmaceutically active agents which are pH dependent and which may be included in the composition include, but are not limited to, weakly basic drugs and their salts that have higher solubilities at lower pH levels. Such drugs include, but are not limited to, guanfacine hydrochloride, guanadrel sulfate, reserpine, anagrelide hydrochloride, propanolol, metoprolol, atenolol, timolol, erthyrthromycin, clonidine, chlorpheniramine, bromopheniramine, diltiazen, and scopolamine. In general, the pharmaceutically active agent is present in the composition in an amount of from about 0.1 wt, % to about 70 wt. %, preferably from about 1 wt. % to about 40 wt %. In one embodiment, the at least one pharmaceutically active agent is guanfacine hydrochloride. In another embodiment, the at least one pharmaceutically active agent is anagrelide hydrocholoride. It is to be understood, however, that the scope of the present invention is not to be limited to any particular pharmaceutically active agent.

Non-pH-dependent sustained release agents which may be included in the composition include, but are not limited to, ethylcellulose, cellulose acetate, vinyl acetate/vinyl chloride copolymers, acrylate/methacrylate copolymers, polyethylene oxide, hydroxypropyl methylcellulose, carrageenan, alginic acid and salts thereof, hydroxyethyl cellulose, hydroxypropyl cellulose, karaya gum, acacia gum, tragacanth gum, locust bean gum, guar gum, sodium carboxymethyl cellulose, methyl cellulose, beeswax, carnauba wax, cetyl alcohol, hydrogenated vegetable oils, and stearyl alcohol. In general, the at least one non-pH-dependent sustained release agent is present in the composition in an amount of from about 5 wt. % to about 50 wt. %, preferably from about 10 wt. % to about 30 wt. %. It is to be understood, however, that the scope of the present invention is not to be limited to any particular non-pH-dependent sustained release agents.

pH-dependent agents that increase the rate of release of the at least one pharmaceutically active agent from the tablet at a pH in excess of 5.5 include, but are not limited to, polymers that swell at a pH in excess of 5.5, and enteric agents, and/or agents that increase the solubility of the at least one pharmaceutically active agent at a pH greater than 5.5, by maintaining an acidic microenvironment in the tablet, e.g., an organic acid. The at least one pH-dependent agent is present in the composition in an amount of from about 0.5 wt. % to about 40 wt. %, preferably from about 1 wt. % to about 20 wt. %.

Polymers that swell at a pH in excess of 5.5 include, but are not limited to, acrylic acid copolymers, sodium alginate, carrageenan, alginic acid, pectin, and sodium carboxymethyl cellulose.

Enteric agents include, but are not limited to, cellulose acetate phthalate, hydroxypropyl methylcellulose phthalate, polyvinyl acetate phthalate, methacrylic acid coplymers, cellulose acetate trimellitate, hydroxypropyl methylcellulose acetate, succinate, shellac, and zein.

Agents that increase the solubility of the at least one pharmaceutically active agent at a pH greater than 5.5 include, but are not limited to, organic acids. Such organic acids maintain an acidic microenvironment in the tablet, and include, but are not limited to, citric acid, fumaric acid, tartaric acid, adipic acid, glucono delta-lactone, and malic acid.

The composition of the present invention may further include other materials such as bulking agents, disintegrating agents, anti-adherants and glidants, lubricants, and binding agents.

Bulking agents include, but are not limited to, microcrystalline cellulose (eg., Avicel®, FMC Corp., Emcocel®, Mendell Inc.), mannitol, xylitol, dicalcium phosphate (eg. Emcompress, Mendell Inc.) calcium sulfate (eg. Compactrol, Mendell Inc.) starches, lactose, sucrose (Dipac, Amstar, and Nutab, Ingredient Technology), dextrose (Emdex, Mendell, Inc.), sorbitol, cellulose powder (Elcema, Degussa, and Solka Floc, Mendell, Inc.) The bulking agent may be present in the composition in an amount of from about 5 wt. % to about 90 wt. %, preferably from about 10 wt. % to about 50 wt. %.

Disintegrating agents which may be included in the composition include, but are not limited to, microcrystalline cellulose, starches, crospovidone (eg. Polyplasdone XL, International Specialty Products.), sodium starch glycolate (Explotab, Mendell Inc.), and crosscarmellose sodium (eg., Ac-Di-Sol, FMC Corp.). The disintegrating agent may be present in the composition in an amount of from about 0.5 wt. % to about 30 wt %, preferably from about 1 wt. % to about 15 wt. %.

Antiadherants and glidants which may be employed in the composition include, but are not limited to, talc, corn starch, silicon dioxide, sodium lauryl sulfate, and metallic stearates. The antiadherant or glidant may be present in the composition in an amount of from about 0.2 wt. % to about 15 wt. %, preferably from about 0.5 wt. % to about 5 wt. %.

Lubricants which may be employed in the composition include, but are not limited to, magnesium stearate, calcium stearate, sodium stearate, stearic acid, sodium stearyl fumarate, hydrogenated cotton seed oil (sterotex), talc, and waxes, including but not limited to, beeswax, carnuba wax, cetyl alcohol, glyceryl stearate, glyceryl palmitate, glyceryl behenate, hydrogenated vegetable oils, and stearyl alcohol. The lubricant may be present in an amount of from about 0.2 wt. % to about 20 wt. %, preferably from about 0.5 wt. % to about 5 wt. %.

Binding agents which may be employed include, but are not limited to, polyvinyl pyrrollidone, starch, methylcellulose, hydroxypropyl methylcellulose, carboxymethyl cellulose, sucrose solution, dextrose solution, acacia, tragacanth and locust bean gum. The binding agent may be present in the composition in an amount of from about 0.2 wt. % to about 10 wt. %, preferably from about 0.5 wt. % to about 5 wt. %.

The compositions of the present invention may be made by a direct compression method, or by a wet granulation method. In the direct compression method, the at least one pharmaceutically active agent and other ingredients are sieved through a stainless steel screen, such as a 40 mesh steel screen. The sieved materials then are charged to a suitable blender, and blended for 10 minutes with an intensifier bar on for 3 minutes. The blend then is compressed into tablets on a rotary press using appropriate tooling. The compressed tablets may be coated, if desired.

In the wet granulation method, the at least one pharmaceutically active agent and other ingredients are granulated with a granulating fluid (e.g., isopropyl alcohol, ethyl alcohol, and water) in a planetary mixer, high shear mixer, or fluidized bed granulator. Binding agents may be contained in the granulating fluid, or may be in the dry mix. The wet granules are dried in an oven or fluidized bed dryer, and then sieved through a suitable screen to obtain free flowing granules. The resulting granules were blended with a suitable lubricant and glidant, and the lubricated granules are compressed into tablets on a rotary press using appropriate tooling. If desired, a coating can be applied onto the compressed tablets.

When the pharmaceutically active agent is guanfacine hydrochloride, the composition may be employed in treating an attention deficit disorder, or attention deficit with hyperactivity disorder. The composition including guanfacine hydrochloride is administered to an animal, such as a mammal, including human and non-human primates, in an amount effective to treat the disorders mentioned hereinabove.

The compositions of the present invention may be employed to treat a variety of diseases or disorders.

When guanfacine hydrochloride is administered as part of a composition in accordance with the present invention, there is a reduction in the number of side effects associated with the administration of guanfacine hydrochloride, or a reduction in the likelihood of side effects associated with the administration of guanfacine hydrochloride.

In accordance with a further aspect of the present invention there is provided a pharmaceutical composition comprising guafancine as an active agent and characterized in that said composition when administered to a patient produces less of the side effects usually associated with guafancine.

In one embodiment the side effects are chosen from Headache, Asthenia, Somnolence, Dizziness, Tacchycardia, Nausea, Pain Abdominal, Infect, Vomit, or Palpitations.

In a further embodiment the side effects are chosen from Headache or Asthenia.

When the pharmaceutically active agent is anagrelide, the composition may be employed in treating a variety of blood disorders, including, but not limited to, myeloproliferative blood disorders or MBDs, such as, for example, essential thrombocythemia, or ET, chronic myelogenous leukemia, or CML, polycythemia vera, or PV, and agnogenic myeloid metaplasia, or AMM. The composition including anagrelide may be administered to an animal, such as a mammal, including human and non-human primates, in an amount effective to treat such disorders.

The active agent anagrelide may be administered to a patient in an amount of from about 0.01 mg to 15 mg, preferably from about 0.1 mg to about 10 mg, more preferably from about 0.1 mg to about 5 mg and most preferably from about 0.5 mg to about 2 mg. In one treatment regimen, anagrelide may be administered to a patient in an amount of 0.5 mg four times a day, or 1 mg twice a day, for at least one week. When anagrelide is administered as part of a composition in accordance with the present invention, there is a reduction in the number of side effects associated with the administration of anagrelide, or a reduction of the likelihood of side effects associated with the administration of anagrelide.

In accordance with a further aspect of the present invention there is provided a pharmaceutical composition comprising anagrelide as an active agent and characterized in that said composition when administered to a patient produces less of the side effects usually associated with anagrelide.

In one embodiment the side effects are chosen from Headache, Asthenia, Somnolence, Dizziness, Tacchycardia, Nausea, Pain Abdominal, Infect, Vomit, or Palpitations.

In a further embodiment the side effects are chosen from Headache or Asthenia.

The invention now will be described with respect to the following examples; however, the scope of the present invention is not intended to be limited thereby.

EXAMPLE 1

Formulations in accordance with the present invention, as well as control formulations, were prepared according to the direct compression described hereinabove. In accordance with such method, guanfacine HCl and other ingredients were sieved through a 40 mesh steel screen. The sieved materials then were charged into a Blendmaster blender (Patterson-Kelley Co.), and blended for 10 minutes with an intensifier bar on for 3 minutes. The blends then are compressed into tablets on a rotary tablet press (Stokes-Merrill Corp., Model 512) using appropriate tooling The formulations are given in Table 1 below

TABLE 1

| Ingredient | PD0052-22A 1* | PD0052-22A 2** | PD0052-25B 1 | PD0052-25B 2 | PD0052-28B 1 | PD0052-28B 2 | PD0052-32B 1 | PD0052-32B 2 | PD0052-32D 1 | PD0052-32D 2 | PD0052-39A 1 | PD0052-39A 2 |
|---|---|---|---|---|---|---|---|---|---|---|---|---|
| Guanfacine HCl | 0.57 | 1.14 | 0.57 | 1.14 | 0.57 | 1.14 | 0.57 | 1.14 | 0.57 | 1.14 | 0.57 | 1.14 |
| Lactose | 37.43 | 74.86 | — | — | — | — | 45.00 | 90.00 | 65.00 | 130.0 | — | — |
| ProSolv | 20.00 | 40.00 | — | — | 30.00 | 60.00 | — | — | — | — | 29.82 | 59.64 |
| Polyox WSR | 40.00 | 80.00 | 40.00 | 80.00 | — | — | 40.00 | 80.00 | 10.00 | 20.00 | — | — |
| Ethocel FP | — | — | — | — | 40.00 | 80.00 | — | — | — | — | 39.82 | 79.64 |
| Cellulose acetate | — | — | 50.00 | 100.00 | — | — | — | — | — | — | — | — |
| Sodium alginate | — | — | — | — | 20.00 | 40.00 | — | — | — | — | — | — |
| Carrageenan | — | — | — | — | — | — | — | — | — | — | 19.91 | 39.82 |
| Carbopol 974P | — | — | — | — | — | — | — | — | 10.00 | 20.00 | — | — |
| Fumaric acid | — | — | — | — | — | — | 5.00 | 10.00 | — | — | — | — |
| Eudragit L100-55 | — | — | — | — | — | — | — | — | 5.00 | 10.00 | — | — |
| EDTA | — | — | — | — | — | — | — | — | — | — | 0.50 | 1.00 |
| Compritol | — | — | 9.43 | 18.86 | 9.43 | 18.63 | 9.43 | 18.63 | 9.43 | 18.63 | 9.37 | 18.74 |
| Stearic acid | 2.00 | 4.00 | — | — | — | — | — | — | — | — | — | — |

*1 = composition in % weight
**2 = composition in mg per tablet
Note:
PD0052-22A and PD0052-25B contain no ionic materials in the formulations. These two formulations serve as a control.
Prosolv is a trade name for silicified microcrystalline cellulose and marketed by Penwest Corp.
Polyox is a trade name for poly(ethyleneoxide) and marketed by Union Carbide.
Carbopol is a trade name for copolymer of acrylic acid and marketed by BF Goodrich.
Ethocel FP is a trade name for ethyl cellulose fine powder grade and marketed by Dow Chemical.
Eudragit L100-55 is a trade name for poly(methacrylic acid, ethyl acrylate) and marketed by Rohm GmbH.
Compritol is a trade name for glyceryl behenate and marketed by Gattefosse.

The dissolution data was determined as follows:

A Vankel dissolution tester (VanKel Industries, Edison, N.J.) was used for all dissolution studies. The apparatus was calibrated according to USP23. The dissolution in 0.1N hydrochloric acid (pH 1.2) or pH 6.8 phosphate buffer was tested using the paddle method (USP Apparatus II), employing 500 ml of dissolution medium at a temperature of 37° C. and an agitation rate of 50 rpm. Samples at specific time points were removed and filtered through a 35 µm filter. The filtered samples were kept in screw cap glass test tubes until analysis. An HPLC system comprised of an autosampler and a pump and a UV detector was used for sample analysis. 50 µl of the dissolution samples were injected directly on the HPLC C18 column using a mixture of acetonitrile and acetate buffer (20:80) as the mobile phase.

The dissolution data are given in Table 2 below.

TABLE 2

Dissolution Data for Guanfacine Sustained Release Tablets

| Time (hour) | PD0052-22A 1* | PD0052-22A 2** | PD0052-25B 1 | PD0052-25B 2 | PD0052-28B 1 | PD0052-28B 2 | PD0052-32B 1 | PD0052-32B 2 | PD0052-32D 1 | PD0052-32D 2 | PD0052-39A 1 | PD0052-39A 2 |
|---|---|---|---|---|---|---|---|---|---|---|---|---|
| 0.5 | 14.0 ± 0.6 | 7.0 ± 1.2 | 13.0 ± 1.5 | 5.0 ± 0.6 | 8.4 ± 2.1 | 10.0 ± 0.6 | 19.0 ± 1.2 | 12.0 ± 0.0 | 31.0 ± 1.2 | 11.0 ± 1.0 | 14.0 ± 0.6 | 10.0 ± 1.0 |
| 1.0 | 24.0 ± 1.0 | 12.0 ± 1.0 | 27.0 ± 2.0 | 7.0 ± 1.0 | 41.0 ± 1.7 | 20.0 ± 1.0 | 31.0 ± 2.6 | 20.0 ± 0.6 | 48.0 ± 1.2 | 19.0 ± 0.6 | 25.0 ± 1.0 | 18.0 ± 2.0 |
| 2.0 | 44.0 ± 0.6 | 19.0 ± 1.5 | 48.0 ± 2.5 | 11.0 ± 0.6 | 64.0 ± 2.5 | 36.0 ± 2.5 | 50.0 ± 4.2 | 35.0 ± 0.6 | 80.0 ± 5.6 | 31.0 ± 1.2 | 42.0 ± 1.0 | 31.0 ± 4.0 |
| 3.0 | 59.0 ± 0.6 | 26.0 ± 1.5 | 63.0 ± 1.7 | 14.0 ± 0.6 | 77.0 ± 2.6 | 49.0 ± 3.6 | 65.0 ± 6.1 | 49.0 ± 1.0 | 96.0 ± 5.0 | 46.0 ± 0.6 | 56.0 ± 2.6 | 46.0 ± 4.4 |
| 4.0 | 71.0 ± 6.0 | 31.0 ± 2.9 | 74.0 ± 1.5 | 16.0 ± 0.6 | 86.0 ± 3.2 | 59.0 ± 3.2 | 77.0 ± 5.5 | 61.0 ± 1.0 | 104 ± 3.5 | 56.0 ± 0.6 | 69.0 ± 3.0 | 56.0 ± 5.8 |
| 6.0 | 90.0 ± 2.0 | 39.0 ± 2.5 | 86.0 ± 1.7 | 19.0 ± 0.0 | 97.0 ± 3.5 | 71.0 ± 5.0 | 99.0 ± 4.4 | 87.0 ± 2.5 | 111 ± 4.0 | 74.0 ± 1.2 | 90.0 ± 2.6 | 72.0 ± 6.2 |
| 8.0 | 99.0 ± 1.7 | 46.0 ± 2.5 | 93.0 ± 2.1 | 21.0 ± 1.0 | 108 ± 3.8 | 80.0 ± 5.5 | 102 ± 1.2 | 97.0 ± 1.5 | 112 ± 4.0 | 89.0 ± 2.3 | 102 ± 2.3 | 83.0 ± 6.4 |
| 12.00 | 105.0 ± 1.5 | 61.0 ± 4.7 | 100.0 ± 1.2 | 25.0 ± 1.0 | 113 ± 3.6 | 91.0 ± 6.0 | 103 ± 2.3 | 98.0 ± 1.0 | 113 ± 3.8 | 107 ± 2.9 | 112 ± 0.6 | 96.0 ± 4.2 |

*1 = percent dissolved using a pH 1.2 dissolution medium
**2 = percent dissolved using a pH 6.8 dissolution medium
Note:
The data represent the mean percent dissolved ± standard deviation of three replicate.

The above results show that the compositions of the present invention have improved dissolution profiles when compared with the control compositions.

EXAMPLE 2

Formulations in accordance with the present invention, as well as control formulations, were prepared according to the direct compression method described hereinabove. In accordance with such method, guanfacine HCl and other ingredients were sieved through a 40 mesh steel screen. The sieved materials then were charged into a Blendmaster blender (Patterson-Kelley Co.), and blended for 10 minutes with an intensifier bar on for 3 minutes. The blends then are compressed into tablets on a rotary tablet press (Stokes-Merrill Corp., Model 512) using appropriate tooling The formulations are given in Table 3 below.

TABLE 3

Weight Percentage of Components in Guanfacine MR Tablets, 1 mg, Batch Numbers 2015.00.001, 2016.00.001 and 2018.00.001

| Component | 2015.00.001 (%) | 2016.00.001 (%) | 2018.00.001 (%) |
|---|---|---|---|
| Guanfacine HCl, USP | 0.57 | 0.57 | 0.57 |
| Hydroxypropryl Methylcellulose (Methocel K4M Premium CR), USP/NF | 10.00 | 15.00 | 5.00 |
| Methacrylic Acid Copolymer (Eudragit L 100-55), USP/NF | 25.00 | — | — |
| Ammonio Methacrylate Copolymer (Eudragit RSPO), USP/NF | — | 25.00 | 22.50 |
| Silicified Microcrystalline Cellulose (Prosolv HD 90) | 25.00 | 20.00 | 34.43 |
| Lactose Monohydrate Povidone Crospovidone Granulated Blend (Ludipress) | 24.43 | 24.43 | 20.00 |
| Fumaric Acid, USP/NF | 5.00 | 10.00 | 5.00 |
| Glyceryl Behenate (Compritol 888 ATO), USP/NF | 10.00 | 5.00 | 12.50 |
| Total | 100.00 | 100.00 | 100.00 |

EXAMPLE 3

Figure 1:
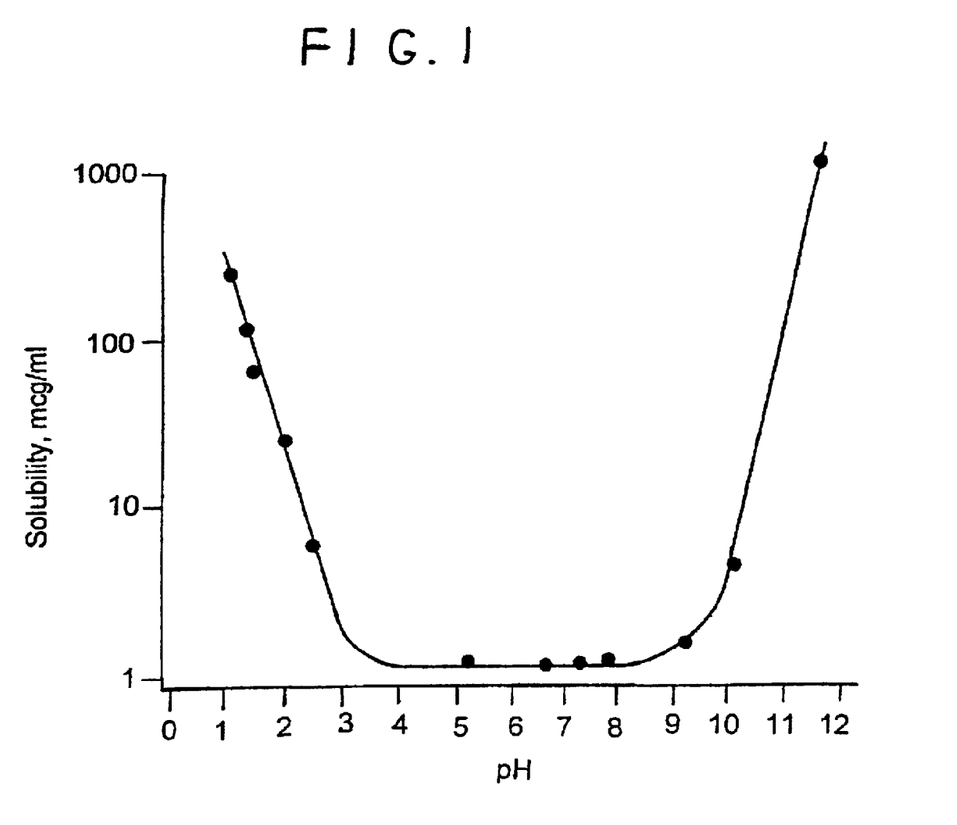
FIG. 1. The solubility-pH profile of anagrelide HCl.

The solubility of anagrelide HCl in aqueous solutions in the pH range of 1 to 11.4 at 25° C. was determined. The solubility-pH profile of anagrelide HCl is shown in FIG. 1. Below pH 3, the solubility increased as the pH decreased which is consistent with formation of a more soluble protonated form. At pH 0.96 the solubility was 236 mcg/mL. Above pH 4, the solubility was independent of pH and remained constant (ca. 1.2 mcg/mL) up to pH 8. Above pH 8, the solubility increased with increasing pH which is due to the ionization of the quinazoline moiety. The solubility at pH 11.4 was 992 mcg/mL.

Formulations I through IV were formulated according to the procedure described in Example 1, except that anagrelide HCl has been substituted for guanfacine HCl.

The formulations are given in Table 4 below.

TABLE 4

| Ingredients | Formulation I mg/Tablet | % | Formulation II mg/Tablet | % | Formulation III mg/Tablet | % | Formulation IV mg/Tablet | % |
|---|---|---|---|---|---|---|---|---|
| Anagrelide HCl | 2.44 (2.0 base) | 1.22 | 2.44 (2.0 base) | 1.22 | 2.44 (2.0 base) | 1.22 | 2.44 (2.0 base) | 1.22 |
| Polyox WSR 301 | 30.00 | 15.00 | 50.00 | 25.00 | | | | |
| Prosolv HD 90 | 60.00 | 30.00 | 60.00 | 30.00 | 66.00 | 33.00 | 80.00 | 40.00 |
| Fujicalin SG* | 60.00 | 30.00 | 30.00 | 15.00 | 60.00 | 30.00 | 40.00 | 20.00 |
| Eudragit L 100-55 | 20.00 | 10.00 | 30.00 | 15.00 | 24.00 | 12.00 | 20.00 | 10.00 |
| Ethocel Std. 100 FP | | | | | 30.00 | 15.00 | | |
| Fumaric Acid | 10.00 | 5.00 | 10.00 | 5.00 | | | | |
| Compritol 888 ATO | 17.56 | 8.78 | 17.56 | 8.78 | 17.56 | 8.78 | 17.56 | 8.78 |
| Polyox WSR N80 | | | | | | | 40.00 | 20.00 |
| Formulation # | PD0073-55A | | PD0073-57A | | PD0073-64A | | PD0073-78A | |
| Total | 200.00 | 100.00 | 200.00 | 100.00 | 200.00 | 100.00 | 200.00 | 100.00 |

*Fujicalin SG is a dibasic calcium phosphate sold by Fuji Chemical Industry Co., Ltd.

A Vankel dissolution tester (VanKel Industries, Edison, N.J.) was used for all dissolution studies. The apparatus was calibrated according to USP 23. The dissolution in 0.1N hydrochloric acid (pH 1.1) with 0.1% Tween 80 or pH 6.8 phosphate buffer with 0.1% Tween 80 was tested using the paddle method (USP Apparatus II), employing 900 ml of dissolution medium at a temperature of 37° C., and an agitation rate of 100 rpm. Samples at specific time points were removed and filtered through a 70 μm filter. The filtered samples were kept in screw cap glass test tubes until analysis. An HPLC system composed of an autosampler and a pump and a UV detector was used for sample analysis. 20 μl of the dissolution samples were injected directly on the HPLC C18 column using a mixture of acetonitrile and ammonium acetate buffer (36:64) as the mobile phase.

The dissolution data are given in Table 5 below.

TABLE 5

Dissolution Data for Anagrelide Sustained Release Tablets

| Time (hour) | PD0073-55A 1* | PD0073-55A 2** | PD0073-57A 1 | PD0073-57A 2 | PD0073-64A 1 | PD0073-64A 2 | PD0073-78A 1 | PD0073-78A 2 |
|---|---|---|---|---|---|---|---|---|
| 0.5  | N/A        | 4.0 ± 0.6  | 6.0 ± 0.0  | 2.0 ± 0.0  | 27.0 ± 2.1 | 5.0 ± 1.0  | 16.0 ± 0.6 | 12.0 ± 1.2 |
| 1.0  | 13.0 ± 0.6 | 6.0 ± 0.0  | 9.0 ± 0.6  | 3.0 ± 0.0  | 39.0 ± 3.1 | 11.0 ± 2.9 | 27.0 ± 1.5 | 30.0 ± 1.0 |
| 2.0  | 21.0 ± 0.6 | 10.0 ± 0.6 | 15.0 ± 0.6 | 7.0 ± 0.0  | 52.0 ± 4.5 | 31.0 ± 3.2 | 43.0 ± 3.6 | 56.0 ± 1.7 |
| 4.0  | 40.0 ± 2.5 | 22.0 ± 1.2 | 30.0 ± 2.3 | 16.0 ± 0.6 | 69.0 ± 5.3 | 58.0 ± 3.5 | 55.0 ± 4.4 | 72.0 ± 1.2 |
| 8.0  | 72.0 ± 5.0 | 57.0 ± 7.4 | 57.0 ± 2.0 | 39.0 ± 1.0 | 85.0 ± 2.6 | 73.0 ± 2.6 | 67 ± 5.5   | 78.0 ± 0.6 |
| 12.0 | 95.0 ± 2.9 | 77.0 ± 5.3 | 77.0 ± 2.1 | 62.0 ± 3.6 | 88.0 ± 1.0 | 79.0 ± 2.1 | 83 ± 3.6   | 82.0 ± 0.0 |

*1 = percent dissolved using a pH 1.1 dissolution medium with 0.1% Tween 80.
**2 = percent dissolved using a pH 6.8 dissolution medium with 0.1% Tween 80.
Note:
The data represent the mean percent dissolved ± standard deviation of three replicates.

EXAMPLE 4

Formulations V, VI, and VII, which are modifications of Formulation IV of Example 2, include the following components as shown in Table 6 below.

TABLE 6

| Component | Formulation V mg/tablet | Formulation V % | Formulation VI mg/tablet | Formulation VI % | Formulaiton VII mg/tablet | Formulaiton VII % |
|---|---|---|---|---|---|---|
| Anagrelide HCl, Monohydrate* | 0.63 | 0.315 | 1.26 | 0.630 | 1.88 | 0.940 |
| Polyethylene Oxide, 60 Mesh, NF (Polyox ™ WSR N80) | 40.00 | 20.000 | 40.00 | 20.000 | 40.00 | 20.000 |
| Dibasic Calcium Phosphate, Anhydrous, USP (Fujicalin SG) | 39.21 | 19.605 | 37.18 | 18.590 | 38.56 | 19.280 |
| Silicified High Density Microcrystalline Cellulose (Prosolv HD 90), USP | 80.00 | 40.000 | 80.00 | 40.000 | 80.00 | 40.000 |
| Methacrylic Acid Copolymer, NF (Eudragit L 100-55) | 20.00 | 10.000 | 20.00 | 10.000 | 20.00 | 10.000 |
| Glyceryl Behenate, NF (Compritol 888 ATO) | 17.56 | 8.780 | 17.56 | 8.780 | 17.56 | 8.780 |
| Magnesium Stearate Powder, NF (Non-Bovine) | 2.00 | 1.000 | 2.00 | 1.000 | 2.00 | 1.00 |
| Green PB-1763 | 0.60 | 0.300 | — | — | — | — |
| Purple PB-1855 | — | — | 2.00 | 1.000 | — | — |
| Total | 200.0 | 100.0 | 200.0 | 100.0 | 200.0 | 100.0 |

*includes 3% overcharge for material loss during processing.

Formulations V, VI, and VII were prepared and processed into tablets according to the following procedure:

Blending

1. Weigh all the ingredients (Prosolv HD90 is divided into 3 portions).
2. Place the ingredients in the order listed below into the V-blender equipped with an intensifier bar:
   a. Prosolv HD90 portion #1
   b. Anagrelide HCl Monohydrate
   c. Green PB-1763 for Formulation V; Purple PB-1855 for Formulation VI strength; no color for Formulation VII
   d. Prosolv HD90 portion #2
3. Blend for 4 minutes in a V-blender with the intensifier bar off. Turn the intensifier bar on and blend for 2 minutes. Turn the intensifier bar off and blend for 4 minutes.
4. Pass the blend through a 30-mesh screen using a Comil at the low speed setting.
5. Pass Prosolv HD90 portion #3 through the same Comil using the 30-mesh screen and low speed.
6. Place the ingredients into the larger V-blender equipped with an intensifier bar in the following order:
   a. Milled Prosolv HD90 from Step 5
   b. Polyox WSR N80, 60 mesh
   c. Milled blend from Step 4 d. Eudragit L100-55
e. Fujicalin SG
7. Blend these ingredients for 4 minutes with intensifier bar off. Turn the intensifier bar on and blend for 2 minutes. Turn the intensifier bar off, add Compritol 888 ATO and blend for 4 minutes.
8. Discharge this blend from the V-blender into a suitable container.
9. Pass Magnesium Stearate through a 30-mesh screen and collect it in a polyethylene bag.
10. Pass the blend from step 8 through a 30-mesh screen using a Comil at the low speed setting and collect it in a polyethylene bag.
11. Transfer the milled blend from step 10 and the Magnesium Stearate from step 9 into the V-blender used in step 7 and mix for 5 minutes with the intensifier bar off.
12. Discharge the blend from step 11 into a polyethylene bag.

Tableting

1. Load the blend into the tablet press hopper.
2. Adjust the tablet weight to 200 mg and the appropriate tablet hardness.
3. Compress the blend into tablets using caplet-shaped tooling.
4. Take tablet samples as required by departmental SOPs to ensure product quality and to complete any process protocols of the tableting process.
5. Run tablets through an appropriate deduster.
6. Collect compressed tablets in a suitable container double lined with clean polyethylene bags.

EXAMPLE 5

Formulations 1, 2, and 3, were prepared, which had the following components in the following amounts, as shown in Table 7 below.

TABLE 7

| | Amount, wt % | | |
|---|---|---|---|
| Component | Formulation 1 | Formulation 2 | Formulation 3 |
| Anagrelide HCl, Monohydrate | 0.61 | 0.61 | 0.61 |
| Polyethylene Oxide (Polyox ™ WSR 301) | 15.00 | — | 25.00 |
| Polyethylene Oxide, 60 Mesh, NF (Polyox ™ WSR N80) | — | 20.00 | — |
| Dibasic Calcium Phosphate, Anhydrous, USP (Fujicalin SG) | 30.61 | 20.61 | 30.61 |
| Silicified High Density Microcrystalline Cellulose (Prosolv HD 90), USP | 30.00 | 40.00 | 15.00 |
| Methacrylic Acid Copolymer (Eudragit L 100-55) | 10.00 | 10.00 | 15.00 |
| Fumaric Acid | 5.00 | — | 5.00 |
| Glyceryl Behenate, NF (Compritol 888 ATO) | 8.78 | 8.78 | 8.78 |
| Total | 100.0 | 100.0 | 100.0 |

The purpose of this example was to assess the bioavailability of three anagrelide HCl extended release tablet formulationsFormulation 1Formulation 2Formulation 3, compared to an immediate release anagrelide HCl formulation (Agrylin®, Lot No. RPA 0002A), following a 1 mg dose, and to determine the safety and tolerability of the extended release formulations in healthy volunteers.

The extent of absorption of each drug ($AUC_{o-t}$) the maximum concentration of drug in plasma ($C_{max}$), and the time of the maximum concentration ($T_{max}$) were evaluated.

Figure 2:
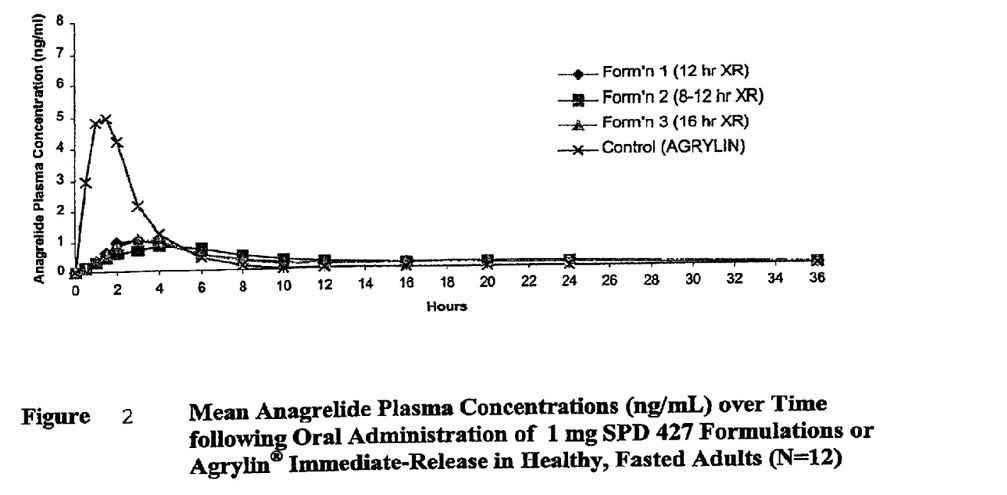
FIG. 2. The mean plasma concentration for anagrelide following dministration of a single 1 mg dose of Agrylin or the anagrelide HCl extended release Formulations 1,2, or 3.

The mean plasma concentrations for anagrelide following administration of a single 1 mg dose of Agrylin®, or the anagrelide HCl extended release Formulations 1, 2, or 3, are given in FIG. 2.

The corresponding pharmacokinetic parameters for each formulation are given in Table 8 below.

TABLE 8

Mean Pharmacokinetic Parameters for Anagrelide

| Treatment | $AUC_{0-inf}$ (ng · hr/mL) | $AUC_{0-t}$ (ng · hr/mL) | $C_{max}$ (ng/mL) | $T_{max}$ (hr) | $T_{width}$ ½$C_{max}$ (hr) |
|---|---|---|---|---|---|
| Formulation 1 | 9.24* | 8.47* | 1.15* | 3.41* | 5.06 |
| Formulation 2 | 10.32* | 9.10* | 1.01* | 3.17* | 5.99 |
| Formulation 3 | 9.41* | 8.48* | 1.17* | 3.46* | 4.30 |
| Agrylin ® | 14.89 | 14.46 | 5.67 | 1.25 | 2.17 |
| | | Bioequivalence | | | |
| Formulation 1: Ratio of test-to-ref. | 0.61 | 0.58 | 0.21 | | |
| 90% CI | 0.49–0.76 | 0.46–0.73 | 0.17–0.27 | | |
| Formulation 2: Ratio of test-to-ref. | 0.59 | 0.53 | 0.17 | | |
| 90% CI | 0.47–0.74 | 0.42–0.67 | 0.14–0.22 | | |
| Formulation 3: Ratio of test-to-ref. | 0.66 | 0.64 | 0.25 | | |
| 90% CI | 0.52 | 0.50–0.81 | 0.20–0.32 | | |

*p < 0.05 compared to Agrylin ® by Dunnett's test

All three experimental formulations exhibited extended release characteristics for drug delivery. The extent of absorption of anagrelide from the experimental formulations relative to immediate-release Agrylin® (ratio of test-to-reference) was 58%, 53% and 64% for the Formulations 1, 2 and 3, respectively.

A measure of the extent of delay in release of active pharmaceutical ingredient of the experimental formulations was the time to reach maximum concentration ($T_{max}$) values observed for anagrelide. The $T_{max}$ values were approximately 2 hours later than that observed for Agrylin®, demonstrating about a 2.6-fold delay in time to reach $C_{max}$ for the three extended release formulations compared with the immediate-release Agrylin®. Furthermore, the length of time at which the anagrelide plasma concentration remained above ½$C_{max}$ ($T_{width}$ ½$C_{max}$) was approximately two- to three-fold greater for the extended release formulations than the immediate release formulation, demonstrating good extended release characteristics.

No serious adverse events were reported. One subject discontinued due to an adverse event (head cold) considered not related to study drug. There were a total of 46 adverse events (AEs) experienced by eleven (11) subjects. The most frequently reported events (>5%), included asthenia, headache, somnolence, and dizziness, and were not unexpected. These events have been reported frequently by the target patient population at large receiving Agrylin® for the treatment of thrombocythemia secondary to all myeloproliferative disorders. Treatment emergent AEs are summarized in Table 9.

TABLE 9

Treatment Emergent AEs

| Preferred Term (Costart) | Count | % (n = 12) |
|---|---|---|
| Asthenia | 12 | 26.1 |
| Headache | 9 | 19.6 |
| Somnolence | 6 | 13.0 |
| Dizziness | 5 | 10.9 |
| Tachycardia | 2 | 4.3 |
| Infection | 2 | 4.3 |
| Nausea | 2 | 4.3 |
| Vomit | 2 | 4.3 |
| Pain Abd | 1 | 2.2 |
| Palpitations | 1 | 2.2 |
| Pain | 1 | 2.2 |
| Hem | 1 | 2.2 |
| Voice alteration | 1 | 2.2 |
| Thirst | 1 | 2.2 |
| Total | 46 | 100.0 |

The data would indicate that adverse events (AEs) observed in subjects following dosage with the extended release formulation were not as prevalent as AEs observed following the immediate release formulation (Agrylin®). More than 50% of the reported AEs were observed following Agrylin® administration. The number of adverse events following administration of the new extended release formulations were 8/46 (17%) for Formulation 1, 9/46 (20%) for Formulation 2, and 4/46 (9%) for Formulation 3 compared to 25/46 (54%) for the marketed Agrylin®. The incidence of subjects reporting adverse events for the new extended-release formulations (4/12 (33%), 6/12 (50%), and 2/12 (17%) for Formulations 1, 2, and 3, respectively) also were substantially lower than the incidence observed in the Agrylin® group (10/12 (83%)). The number and percentage of subjects reporting adverse events are presented in Table 10.

TABLE 10

Treatment Emergent Adverse Events per Treatment Group

| Drug Treatment | Preferred Term (Costart) | No. Subjects Reporting | % Subjects Reporting | No. AEs Reported |
|---|---|---|---|---|
| Formulation 1 (n = 12) | Asthenia | 3 | 25.0 | 3 |
| | Nausea | 1 | 8.3 | 1 |
| | Pain | 1 | 8.3 | 1 |
| | Somnolence | 1 | 8.3 | 1 |
| | Thirst | 1 | 8.3 | 1 |
| | Vomit | 1 | 8.3 | 1 |
| Formulation 2 (n = 12) | Asthenia | 3 | 25.0 | 3 |
| | Dizziness | 2 | 16.7 | 2 |
| | Headache | 2 | 16.7 | 2 |
| | Somnolence | 1 | 8.3 | 1 |
| | Hem | 1 | 8.3 | 1 |
| Formulation 3 (n = 11) | Asthenia | 1 | 9.3 | 1 |
| | Headache | 1 | 9.3 | 1 |
| | Infect | 1 | 9.3 | 1 |
| | Voice alteration | 1 | 9.3 | 1 |
| Agrylin ® (n = 12) | Headache | 6 | 50.0 | 6 |
| | Asthenia | 5 | 41.7 | 5 |
| | Somnolence | 3 | 25.0 | 4 |
| | Dizziness | 3 | 25.0 | 3 |
| | Tacchycardia | 2 | 16.7 | 2 |
| | Nausea | 1 | 8.3 | 1 |
| | Pain Abdominal | 1 | 8.3 | 1 |
| | Infect | 1 | 8.3 | 1 |
| | Vomit | 1 | 8.3 | 1 |
| | Palpitations | 1 | 8.3 | 1 |
| Total (n = 12) | | | | 46 |

With respect to clinical laboratory and physical examination findings, statistically significant (p<0.01) increases in pulse compared with baseline were observed with Agrylin® at 2, 4, and 24 hours post dose. Significant increases were observed at 24 hours post dose for Formulations 1 and 3. Only Agrylin® showed a statistically significant changed from baseline for blood pressure (i.e. at 24 hours post dose for diastolic blood pressure).

It is to be understood, however, that the scope of the present invention is not to be limited to the specific embodiments described above. The invention may be practiced other than as particularly described and still be within the scope of the accompanying claims.

What is claimed is:

1. A pharmaceutical composition, comprising:
   (a) guanfacine;
   (b) hydroxypropyll methylcellulose;
   (c) ammonip methacrylate copolymer;
   (d) microcrystalline cellulose;
   (e) a methacrylic acid copolymer;
   (f) glycejyl behenate;
   (g) fumaric acid;
   (h) lactose monohydrate;
   (i) povidone; and
   (j) crospovidope aranulated blend.

2. A pharmaceutical composition, comprising:
   (a) quanfacine hydrochloride;
   (b) hydroxypropyl methylcellulose;
   (c) ammonio methacrylate copolymer;
   (d) microcrystalline cellulose;
   (e) a methacrylic acid polymer;
   (f) glyceryl behenate;

(g) fumaric acid;

(h) lactose monohydrate;

(i) povidone; and (j) crospovidone granulated blend.

3. A method for treating an attention deficit disorder or attention deficit with hyperactivity disorder in a patient, comprising administering to said patient a composition comprising (a) at least one pharmaceutically active agent that is pH dependent, said pharmaceutically active agent being quanfacine or quanfacine hydrochloride;

(b) at least one non-pH dependent sustained release agent selected from the group consisting of ethylcellulose, cellulose acetate, vinyl acetate/vinyl chloride copolymer, acrylate/methacrylate copolymers, polvethylene oxide, hydroxynropyl methylcellulose, carageenan, alginic acid and salts thereof, hvdroxyethyl cellulose, hydroxypropyl cellulose, karaya gum, acacia gum, tragacanth gum, locust bean gum, guar gum, sodium carboxymethyl cellulose, methyl cellulose, beeswax, camauba wax. cetyl alcohol, hydrogenated vegetable oils, and stearyl alcohol; and (c) at least one pH dependent agent that increases the rate of release of said at least one pharmaceutlcally active apent from a tablet dosage form at a pH in excess of 5.5;

which is given in an amount effective to treat said attention deficit disorder or attention deficit with hyperactivity disorder in said patient.

4. The method of claim 3, wherein said at least pH-dependen agent is at least one polymer that swells at a pH in excess of 5.5.

5. The method of claim 4, wherein said at least one polymer that swells at a pH in excess of 5.5 is selected from acrylic acid polymers, sodium alginate, carrageenan, alginic acid, pectin, or sodium carboxymethylcellulose.

6. The method of claim 3, wherein said at least one pH-dependent agent is at least one enteric agent.

7. The method of claim 3, wherein said enteric agent is select from cellulose acetate phthalate, hydroxypropyl methylcellulose phthalate, polvinyl acetate phthalate, methacrylic acid copolymers, cellulose acetate trimellitate, hydroxypropyl methylcellulose acetate, succinate, shellac, or zein.

8. A method of reducing the likelihood of side effects associated with the administration of guanfacine, comprising administering to a patient a therapeutically effective amount of a the position comprising (a) at least one pharmaceutically active agent that is pH dependent, said pharmaceutically active agent being guanfacine or guanfacine hydrochloride;

(b) at least one non-pH dependent sustained release agent selected from the group consisting of ethylcellulose, celluipse acetate, vinyl acetate/vinyl chloride copolymers, acrylate/methacrylate copolymers, polyethylene oxide, hydroxynropyl methylcellulose, carageenan, glainic acid and salts thereof, hydroxyethyl cellulose, hydroxypropyl cellulose, karaya gum, acacia gum, tragacanth gum, locust bean gum, guar gum, sodium carboxymethyl cellulose, methyl cellulose, beeswax, carnauba wax, cetyl alcohol, hydrogenated vegetable oils, and stearyl alcohol; and (c) at least one pH dependent agent that increases the rate of release of said at least one pharmaceutically active agent from a tablet dosage form at a pH in excess of 5.5.

9. The method of clalm 8, wherein said at least one pH-dependent gent is at least one polymer that swells at a pH In excess of 5.5.

10. The method of claim 9, wherein said at least one polymer at swells at a pH in excess of 5.5 is selected from acrylic acid polymers, sodium alginate, carrageenan, alginic acid, pectin, or sodium carboxymethylcellulose.

11. The method of claim 8, wherein said at least one pH-dependent agent is at least one enteric agent.

12. The method of claim 11, wherein said entetic agent is select from cellulose acetate phthalate, hydroxypropyl methyicellulose phthalate, polvinyl acetate phthalate, methacrylic acid copolymers, cellulose acetate trimellitate, hydroxypropyl methyloellulose acetate, succinate, shellac, or zein.

\* \* \* \* \*